(12) United States Patent
Minar (10) Patent No.: US 11,779,643 B2
(45) Date of Patent: Oct. 10, 2023

(54) METHODS AND COMPOSITIONS FOR THE TREATMENT OF AN INFLAMMATORY BOWEL DISEASE

(71) Applicant: Children's Hospital Medical Center, Cincinnati, OH (US)

(72) Inventor: Phillip Minar, Montgomery, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 12 days.

(21) Appl. No.: 17/004,555

(22) Filed: Aug. 27, 2020

(65) Prior Publication Data
US 2021/0060162 A1 Mar. 4, 2021

Related U.S. Application Data

(60) Provisional application No. 62/892,813, filed on Aug. 28, 2019.

(51) Int. Cl.
| | | |
|---|---|---|
| A61K 39/395 | (2006.01) | |
| A61K 31/573 | (2006.01) | |
| A61K 39/00 | (2006.01) | |
| A61P 1/00 | (2006.01) | |
| C07K 16/24 | (2006.01) | |
| G01N 33/68 | (2006.01) | |

(52) U.S. Cl.
CPC ...... *A61K 39/39558* (2013.01); *A61K 31/573* (2013.01); *A61P 1/00* (2018.01); *C07K 16/241* (2013.01); *G01N 33/6863* (2013.01); *A61K 2039/505* (2013.01); *C07K 2317/24* (2013.01); *G01N 2333/52* (2013.01); *G01N 2800/065* (2013.01)

(58) Field of Classification Search
CPC combination set(s) only.
See application file for complete search history.

(56) References Cited

U.S. PATENT DOCUMENTS

| | | | |
|---|---|---|---|
| 8,236,752 B1 | 8/2012 | Sung et al. | |
| 2009/0054253 A1 * | 2/2009 | Li | C12Q 1/6883 435/6.16 |
| 2017/0166638 A1 * | 6/2017 | Hristodorov | A61P 1/16 |

FOREIGN PATENT DOCUMENTS

WO WO-2016120625 A1 * 8/2016 ............. A61K 31/56

OTHER PUBLICATIONS

Minar et al (Elevated Preteratmetn Plasma Oncostatin M Is Associated with Poor Biochemical Response to Infliximab, Crohn's and Colitis 360, vol. 1, Published: Aug. 19, 2019) (Year: 2019).*
West et al (Oncostatin M drives intestinal inflammation in mice and its abundance predicts response to tumor necrosis factor-neutralizing therapy in patients with inflammatory bowel disease, Nat. Med, vol. 23, 2017) (Year: 2017).*
Arijs, I., et al., "Predictive Value of Epithelial Gene Expression Profiles for Response to Infliximab in Crohn's Disease," Inflamm Bowel Dis, 2010, 16(12):2090-2098, 9 pgs.
Arnott, I.D.R., et al., "An analysis of factors influencing short-term and sustained response to infliximab treatment for Crohn's disease," Aliment Pharmacol Ther, 2003, 17:1451-1457, 7 pgs.
Ballengee, C.R., et al., "Association Between Plasma Level of Collagen Type III alpha 1 Chain and Development of Strictures in Pediatric Patients with Crohn's Disease," Clin Gastroenterol Hepatol, 2019, 17(9):1799-1806, 19 pgs.
Clarkston, K., et al., "Development of Infliximab Target Concentrations During Induction in Pediatric Crohn Disease Patients," J Pediatr Gastroenterol Nutr, 2019, 69:68-74, 7 pgs.
Colombel, J-F., et al., "Effect of tight control management on Crohn's disease (CALM): a multicentre, randomised, controlled phase 3 trial," Lancet, 2017, 390:2779-2789, 11 pgs.
D'Arcangelo, G., et al., "Predictors of Long-Term Clinical and Endoscopic Remission in Children With Crohn Disease Treated With Infliximab," J Pediatr Gastroenterol Nutr, 2019, 68:841-846, 6 pgs.
D'Haens, G., et al., "Fecal Calprotectin is a Surrogate Marker for Endoscopic Lesions in Inflammatoiy Bowel Disease," Inflamm Bowel Dis, 2012, 18:2218-2224, 7 pgs.
D'Haens, G., et al., "Increasing Infliximab Dose Based on Symptoms, Biomarkers, and Serum Drug Concentrations Does Not Increase Clinical, Endoscopic, and Corticosteroid-Free Remission in Patients With Active Luminal Crohn's Disease," Gastroenterology, 2018, 154:1343-1351, 10 pgs.
Gaujoux, R., et al., "Cell-centred meta-analysis reveals baseline predictors of anti-TNFα non-response in biopsy and blood of patients with IBD," Gut, 2019, 68:604-614, 11 pgs.
Guiotto, C., et al., "Clinical relevance and inter-test reliability of anti-infliximab antibodies and infliximab trough levels in patients with inflammatory bowel disease," Dig Liver Dis, 2016, 48:138-143, 6 pgs.
Haberman, Y., et al., "Pediatric Crohn disease patients exhibit specific ileal transcriptome and microbiome signature," J Clin Invest, 2014, 124(8):3617-3633, 17 pgs.
Hyams, J., et al., "Induction and Maintenance Infliximab Therapy for the Treatment of Moderate-to-Severe Crohn's Disease in Children," Gastroenterology, 2007 132:863-873; 11 pgs.
Hyams, J.S., et al., "Safety and Efficacy of Adalimumab for Moderate to Severe Crohn's Disease in Children," Gastroenterology, 2012, 143:365-374.e2, 12 pgs.

(Continued)

*Primary Examiner* — Laura B Goddard
*Assistant Examiner* — Sarah A Alsomairy
(74) *Attorney, Agent, or Firm* — FROST BROWN TODD LLP (57) ABSTRACT

Disclosed herein are methods for the treatment of an individual having an inflammatory bowel disease ("IBD"). The disclosed methods may include the detection of Oncostatin M (OSM) in a biological sample obtained from an individual having an IBD. The detection of OSM may be used to characterize the individual as a tumor necrosis factor (TNF) inhibitor (TNFi) responder or a TNFi non-responder for selection of appropriate treatment.

14 Claims, 7 Drawing Sheets

(56) References Cited

OTHER PUBLICATIONS

Kang, B., et al., "Mucosal Healing in Paediatric Patients with Moderate-to-Severe Luminal Crohn's Disease Under Combined Immunosuppression: Escalation versus Early Treatment," J Crohns Colitis, 2016, pp. 1279-1286, 8 pgs.

Kelsen, J.R., et al., "Infliximab Therapy in Pediatric Patients 7 Years of Age and Younger," J Pediatr Gastroenterol Nutr, 2014, 59:758-762, 5 pgs.

Kennedy, N.A., et al., "Predictors of anti-TNF treatment failure in anti-TNF-naive patients with active luminal Crohn's disease: a prospective, multicentre, cohort study," Lancet Gastroenterol Hepatol, 2019, 4:341-353, 13 pgs.

Kugathasan, S., et al., "Prediction of complicated disease course for children newly diagnosed with Crohn's disease: a multicentre inception cohort study," Lancet, 2017, 389:1710-1718, 9 pgs.

Louis, E., et al., "A Positive Response to Infliximab in Crohn Disease: Association with a Higher Systemic Inflammation Before Treatment But Not With -308 TNF Gene Polymorphism," Scand J Gastroenterol, 2002, 37:818-824, 8 pgs.

Louis, E., "Fecal calprotectin: towards a standardized use for inflammatory bowel disease management in routine practice," J Crohns Colitis, 2015, pp. 1-3, 3 pgs.

Minar, P., et al., "Utility of Neutrophil Fcγ Receptor I (CD64) Index as a Biomarker for Mucosal Inflammation in Pediatric Crohn's Disease," Inflamm Bowel Dis, 2014, 20(6):1037-1048, 23 pgs.

Minar, P., et al., "A Low Neutrophil CD64 Index is Associated with Sustained Remission during Infliximab Maintenance Therapy," Inflamm Bowel Dis, 2016, 22(11):2641-2647, 17 pgs.

Minar, P., et al., "Validation of Neutrophil CD64 Blood Biomarkers to Detect Mucosal Inflammation in Pediatric Crohn's Disease," Inflamm Bowel Dis, 2018, 24(1):198-208, 11 pgs.

Nancey, S., et al., "Neopterin is a Novel Reliable Fecal Marker as Accurate as Calprotectin for Predicting Endoscopic Disease Activity in Patients with Inflammatory Bowel Diseases," Inflamm Bowel Dis, 2013, 19:1043-1052, 10 pgs.

Papamichael, K., et al., "Proactive Infliximab Monitoring Following Reactive Testing is Associated With Better Clinical Outcomes Than Reactive Testing Alone in Patients With Inflammatory Bowel Disease," J Crohns Colitis, 2018, pp. 804-810, 7 pgs.

Singh, N., et al., "Early Infliximab Trough Levels Are Associated with Persistent Remission in Pediatric Patients with Inflammatory Bowel Disease," Inflamm Bowel Dis, 2014, 20:1708-1713, 6 pgs.

Tanaka, M., et al., "Oncostatin M, a multifunctional cytokine," Rev Physiol Biochem Pharmacol, 2003, 149:39-52, 14 pgs.

Tew, G.W., et al., "Association Between Response to Etrolizumab and Expression of Integrin αE and Granzyme A in Colon Biopsies of Patients With Ulcerative Colitis," Gastroenterology, 2016, 150(2):477-487.e9, 20 pgs.

Turner, D., et al., "Mathematical Weighting of the Pediatric Crohn's Disease Activity Index (PCDAI) and Comparison with its Other Short Versions," Inflamm Bowel Dis, 2012, 18:55-62, 8 pgs.

Turner, D., et al., "Which PCDAI Version Best Reflects Intestinal Inflammation in Pediatric Crohn Disease?" J Pediatr Gastroenterol Nutr, 2017, 64:254-260, 7 pgs.

Van Assche, G., et al., "Switch to adalimumab in patients with Crohn's disease controlled by maintenance infliximab: prospective randomised Switch trial," Gut, 2012, 61:229-234, 6 pgs.

Vermeire, S., et al., "Demographic and Clinical Parameters Influencing the Short-Term Outcome of Anti-Tumor Necrosis Factor (Infliximab) Treatment in Crohn's Disease," Am J Gastroenterol, 2002, 97(9):2357-2363, 7 pgs.

Verstockt, B., et al., "Low TREM1 expression in whole blood predicts anti-TNF response in inflammatory bowel disease," EBioMedicine, 2019, 40:733-742, 10 pgs.

West, N.R., et al., "Oncostatin M drives intestinal inflammation and predicts response to tumor necrosis factor-neutralizing therapy in patients with inflammatory bowel disease," Nat Med, 2017, 23(5):579-589, 14 pgs.

Wojtal, K.A., et al., "Fc Gamma Receptor CD64 Modulates the Inhibitory Activity of Infliximab," PLoS One, 2012, 7(8):e43361, 15 pgs.

Wu, J., et al., "Serum Protein Biomarkers of Fibrosis Aid in Risk Stratification of Future Stricturing Complications in Pediatric Crohn's Disease," Am J Gastroenterol, 2019, 114:777-785, 9 pgs.

Zubin, G., et al., "Predicting Endoscopic Crohn's Disease Activity Before and After Induction Therapy in Children: A Comprehensive Assessment of PCDAI, CRP, and Fecal Calprotectin," Inflamm Bowel Dis, 2015, 21:1386-1391, 6 pgs.

* cited by examiner

FIG. 5C

METHODS AND COMPOSITIONS FOR THE TREATMENT OF AN INFLAMMATORY BOWEL DISEASE

CROSS-REFERENCE TO RELATED APPLICATIONS

This application claims priority to and benefit of U.S. Provisional Patent Ser. No. 62/892,813, filed Aug. 28, 2019 to Minar, the contents of which are incorporated in their entirety for all purposes.

STATEMENT REGARDING FEDERALLY-SPONSORED RESEARCH

This invention was made with government support under DK105229 awarded by the National Institutes of Health. The government has certain rights in the invention.

BACKGROUND

Therapeutic options for moderate-to-severe Crohn Disease (CD) include monoclonal antibodies (mAb) that antagonize circulating or tissue-bound inflammatory cytokines and leukocyte recruitment pathways. Following the pivotal REACH study,[1] mAb's targeting tumor necrosis factor-alpha (anti-TNF) have become and remain the most commonly used first-line biologic agents for children with moderate-to-severe CD. Despite high rates of clinical response to anti-TNF (75%-88.4%),[1, 2] many children and adults continue to experience symptom flares and serious disease complications as rates of mucosal healing range between 36% and 46% with only 19%-36% achieving deep remission (both clinical remission and mucosal healing).[3, 4] Although rates of deep remission are likely to improve with increased utilization of personalized anti-TNF dosing regimens[5] and effective dose optimization strategies following proactive therapeutic drug monitoring,[6] a sizable percentage of children will continue to fail anti-TNF despite adequate drug exposure. Despite the heterogeneity of CD phenotypes and a potentially aggressive course of inadequately treated CD, treatment selection is currently based on clinical factors that poorly define CD subtype. Thus, there is a need in the art for improved methods for the selection of treatment of individuals having CD, including methods that help to identify and stratify patients that may respond to certain therapeutics preferentially.

BRIEF SUMMARY

Disclosed herein are methods for the treatment of an individual having an inflammatory bowel disease ("IBD"). The disclosed methods may include the detection of Oncostatin M (OSM) in a biological sample obtained from an individual having an IBD. The detection of OSM may be used to characterize the individual as a tumor necrosis factor (TNF) inhibitor (TNFi) responder or a TNFi non-responder for selection of appropriate treatment.

BRIEF DESCRIPTION OF THE DRAWINGS

This application file may contain at least one drawing executed in color. Copies of this patent or patent application publication with color drawing(s) will be provided by the Office upon request and payment of the necessary fee. Those of skill in the art will understand that the drawings, described below, are for illustrative purposes only. The drawings are not intended to limit the scope of the present teachings in any way.

FIG. 1A-1B.

FIG. 2A-2B. Study participants were either classified as $OSM^{high}$ or $OSM^{low}$ based on their pretreatment plasma OSM level ($\geq 143.5$ pg/mL=$OSM_{high}$).

FIG. 3A-3B.

FIG. 4A-4D. Repeat plasma OSM was available in 30/35 patients that were assessed for the primary outcome with a repeat nCD64 available in 29/35 patients.

FIG. 5A-5C. Evaluation of W12 infliximab concentrations in early (FIG. 5A) responders (>50% reduction in baseline fecal calprotectin) and non-responders and (FIG. 5B) remitters (fecal calprotectin $\leq 250$ µg/g) and non-remitters.

DETAILED DESCRIPTION

Definitions

Unless otherwise noted, terms are to be understood according to conventional usage by those of ordinary skill in the relevant art. In case of conflict, the present document, including definitions, will control. Preferred methods and materials are described below, although methods and materials similar or equivalent to those described herein may be used in practice or testing of the present invention. All publications, patent applications, patents and other references mentioned herein are incorporated by reference in their entirety. The materials, methods, and examples disclosed herein are illustrative only and not intended to be limiting.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" may mean within 1 or more than 1 standard deviation, per the practice in the art. Alternatively, "about" may mean a range of up to 20%, or up to 10%, or up to 5%, or up to 1% of a given value. Alternatively, particularly with respect to biological systems or processes, the term may mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "effective amount" means the amount of one or more active components that is sufficient to show a desired effect. This includes both therapeutic and prophylactic effects. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some embodiments, the terms refer to humans. In further embodiments, the terms may refer to children.

Measuring/analyzing/quantifying the level of a biomarker provided herein, may be performed using methods know in the art. For example, methods to determine the level of a biomarker include, but are not limited to, PCR, microarray assays, immunoblots, northern blots, ELISA, fluorescence-based methods (immunofluorescence, FACS), mass spectrometry, and the like.

As used herein, the term "expression" refers to the transcription and stable accumulation of sense (mRNA) or antisense RNA derived from a nucleic acid fragment or fragments. Expression also refers to the translation of mRNA into a polypeptide. Biomarker expression may be tissue-specific. Biomarker expression may be global. Biomarker expression may be systemic.

As used herein, "biological sample" refers to blood, serum, plasma, sperm, urine, mucous, tissue biopsy, organ biopsy, synovial fluid, urine, bile fluid, cerebrospinal fluid, saliva, mucosal secretion, effusion, sweat and combinations thereof. For example, a biological sample may be cells, tissue, peripheral blood, a body fluid and the like. It is understood that a biological sample includes one obtained from a normal subject.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

Determining the expression of a disclosed biomarker may include assessing gene product or protein abundance. Protein abundance reflects gene expression profiles, which may be determined, by methods known in the art, such as, but not limited to Western blot analysis, RIA, ELISA, HPLC, functional assays, such as enzymatic assays, as applicable, and others. An expression profile may be determined by a change in mRNA levels, surface expression, secretion, or other partitioning of a polypeptide.

As used herein, the term "measuring" refers to methods which include one or more of detecting the presence or absence of a biomarker in a sample, quantifying the amount of marker(s) in the sample, with or without reference to a control value. Measuring can be accomplished by methods known in the art and those further described herein.

"Solid support" refers to a solid material which can be derivatized with, or otherwise attached to, a capture reagent. Exemplary solid supports include probes, microtiter plates and chromatographic resins.

As used herein, "increased expression" or "increase in level or "elevated level" refer to an increase in the level of a biomarker relative to the level or activity of the biomarker in a standard. An increase in level may refer to between a 10 to about a 1000% increase in biomarker levels in a biological sample. The increase of a biological maker level taken from an individual may be 1-10%, 11-20%, 21-30%, 31-40%, 41-50%, 51-60%, 61-70%, 71-80%, 81-90%, 91-150%, 151-1000% elevated over the levels of that biomarker taken from a normal subject (standard).

Pre-treatment (and during treatment) elevations of peripheral blood (plasma) Oncostatin M are associated with treatment non-response to drugs (monoclonal antibodies) that antagonize tumor necrosis factor-alpha (TNF) in patients with inflammatory bowel disease. Measuring Oncostatin M ("OSM", or alternatively, as described herein, a biomarker) from the peripheral blood, either before starting an anti-TNF treatment as a companion diagnostic, or during anti-TNF treatment, as a pharmacodynamic biomarker useful for improving management of patients with inflammatory bowel disease.

In one aspect, a method of treating an individual having an inflammatory bowel disease ("IBD") is disclosed. The method may comprise the steps of a) detecting a level of Oncostatin M (OSM) protein in a biological sample obtained from said individual; b) characterizing said individual as a tumor necrosis factor (TNF) inhibitor (TNFi) responder or a TNFi non-responder; and c) treating said TNFi responder with a TNF inhibitor (TNFi). A responder and remitter will generally be treated in the same manner, while a remitter and nonremitter may or may not be treated the same way and nonresponders and nonremitters may not be treated the same. Primary nonresponders are generally patients that, regardless of the treatment, will not respond to the medication. A non-remitter is a patient that has not yet had complete healing, but are capable of healing. Primary non-responders may never heal.

In one aspect, the IBD may be selected from ulcerative colitis (UC) and Crohn's disease (CD). UC and CD are treated similarly and may have similar immune responses. In certain aspects, the IBD may be a patient having inflammation localized to the colon (Crohn's colitis).

In one aspect, the biological sample from which the detection of OSM is carried out, is one or more of blood, serum, and plasma obtained from said individual. Exemplary biological fluid samples taken from a subject include blood, serum, plasma, urine, tears, saliva etc. In some aspects, the sample can be diluted with a suitable eluant before detecting the level of OSM in the sample.

In one aspect, the detecting may comprise contacting the biological sample with an antibody that specifically binds to OSM protein, followed by measurement of an amount of OSM bound to the antibody. The assaying may comprise measuring the amount of the antibody-OSM complex. The detecting may comprise determining OSM concentrations using an enzyme-linked immunosorbent assay (ELISA) and said biological sample is serum or plasma.

In one aspect, the method may comprise comparing the measured OSM protein to a control, and further, optionally, normalizing the measured OSM to the control. In certain aspects, the meaning and subsequent treatment indication of an elevated OSM value as compared to that of a normal individual not presenting or diagnosed with an IBD will be readily appreciated by one of ordinary skill in the art, in view of Applicant's teachings herein. That is, an elevated OSM indicates that an individual is a non-responder. In certain aspects, a value may be indicative. Specifically, in certain aspects, using an enzyme-linked immunosorbent assay (ELISA) assay and a plasma sample from an individual, a value of at least >50 pg/ml indicates a likelihood that an individual is a non-responder, whereas a level that is closer to undetectable (<10 pg/ml) suggests that an individual is a responder (i.e., more likely to have a possible response to a TNF inhibitor). In certain aspects, an individual may be characterized as a responder when a pre-infliximab plasma OSM of greater than about 40 pg/mL, or greater than about 50 pg/mL, or greater than about 60 pg/mL, or greater than about 70 pg/mL, or greater than about 80 pg/mL, or greater than about 90 pg/mL, or greater than about 100 pg/mL is detected.

By TNFi, it is meant any anti-TNF treatment, which may include a biologic, for example an antibody as known in the art, which is specific to TNF and inhibits activity. In one aspect, the TNFi may be an anti-TNF antibody, or more particularly, an anti-TNF monoclonal antibody. In certain aspects, the TNFi may be selected from Adalimumab (Humira®), adalimumab-atto (Amjevita™) Certolizumab pegol (Cimzia®), Etanercept (Enbrel®), Golimumab (Simponi®, Simponi Aria®), and Infliximab (Remicade®), Infliximab-axxq (Avsola™), Adalimumab-adaz (Hymiroz™), infliximab-dyyb (Inflectra™), Renflexis (infliximab biosimilar), or any biosimilar thereof.

Exemplary, non-limiting TNF inhibitors are described in the art, for example, U.S. Pat. No. 8,236,752 as follows: Adalimumab (brand name HUMIRA) is a TNF inhibitor that binds to TNFα, preventing it from activating TNF receptors. Adalimumab is constructed from a fully human monoclonal antibody. Adalimumab has a chemical formula of $C_{6428}H_{9912}N_{1694}O_{1987}S_{46}$ and a molecular mass of 144190.3 g/mol; Etanercept (Enbrel) is a recombinant-DNA drug made by combining two proteins (a fusion protein) that links human soluble TNF receptor to the Fc component of human immunoglobulin G1 (IgG1) and acts as a TNF inhibitor. Etanercept has a chemical formula of $C_{2224}H_{3475}N_{621}O_{698}S_{36}$ and a molecular mass of 51234.9 g/mol. Etanercept binds to TNFα and is reported to decrease its role in disorders involving excess inflammation in humans and other animals, including autoimmune diseases such as ankylosing spondylitis, juvenile rheumatoid arthritis, psoriasis, psoriatic arthritis, rheumatoid arthritis, and, potentially a variety of other disorders mediated by excess TNFα; Infliximab (brand name Remicade) is a chimeric monoclonal antibody that includes both mouse (murine) and human components (i.e. murine binding $F_{ab}$ domains and human constant $F_c$ domains). The drug blocks the action of the pleiotropic proinflammatory TNFα (tumor necrosis factor alpha) by binding to it and preventing it from signaling the receptors for TNFα on the surface of cells. TNFα is one of the key cytokines that triggers and sustains the inflammation response. Infliximab has a chemical formula $C_{6428}H_{9912}N_{1694}O_{1987}S_{46}$ and a molecular mass of 144190.3 g/mol. Remicade and Humira are "anti-TNF antibodies", and neutralize extracellular, transmembrane, and receptor-bound TNF alpha. Enbrel, also a TNF antagonist, is a receptor-construct fusion protein. One of ordinary skill in the art will readily appreciate TNF inhibitors useful for the disclosed methods.

In one aspect, the individual, applying the methods set forth herein, may be characterized as a non-responder. In this aspect, the individual may be administered a non-TNFi therapy. For example, suitable therapies may include, one or more active selected from vedolizumab (Entyvio™), ustekinumab (Stelara®), tofacitinib (Xelijanz®), mesalamine, budesonide, Prednisone. 6-mercaptopurine, azathioprine, methotrexate, and combinations thereof.

In one aspect, the individual, applying the methods set forth herein, may be characterized as a non-responder, and may be administered a TNFi at a dose that is higher that the recommended dose for said TNFi.

In a further aspect, the methods may further include detecting CD64 in said biological sample, wherein an elevated CD64 level is predictive of a poor response to anti-TNF therapy.

In one aspect, a method of diagnosing and treating inflammatory bowel disease ("IBD") in an individual in need thereof is disclosed. In this aspect, the method may comprise a) establishing, using a computing system, a model for identifying an individual likely to respond to a TNF inhibitor (TNFi), by using expression level data of an OSM biomarker; b) contacting a biological sample from said individual with at least one detection agent capable of specifically binding to OSM; c) acquiring expression level from the biomarker measured from the biological sample of the individual; d) diagnosing said individual as one or more of a responder, remitter, non-responder, and non-remitter; and e) administering a therapy to said individual. In this aspect, if an individual is determined to be a responder or a remitter, the individual is administered a TNFi therapy, such as an anti-TNF antibody, an anti-TNF monoclonal antibody, or one or more of Adalimumab (Humira®), adalimumab-atto (Amjevita™) Certolizumab pegol (Cimzia®), Etanercept (Enbrel®), Golimumab (Simponi®, Simponi Aria®), and Infliximab (Remicade®), Infliximab-axxq (Avsola™), Adalimumab-adaz (Hymiroz™), infliximab-dyyb (Inflectra™), Renflexis (infliximab biosimilar), or any biosimilar thereof. Alternatively, if, using the methods disclosed herein, said individual is determined to be a non-responder or a non-remitter, said individual is administered a non-TNFi therapy, for example, one or more active agent selected from vedolizumab (Entyvio™), ustekinumab (Stelara®), tofacitinib (Xelijanz®), mesalamine, budesonide, Prednisone. 6-mercaptopurine, azathioprine, methotrexate, and combinations thereof.

In a yet further aspect, disclosed herein is an in vitro method for the diagnosis, prognosis, stratification and/or monitoring of inflammatory bowel disease in a human subject. The method may comprise the steps of a) detecting a level of OSM protein in a blood or plasma sample obtained from the human subject, wherein a higher level of OSM in the blood or plasma sample from the human subject compared to a reference value (such as that of a control subject that does not have an IBD) is indicative as being a successful candidate for TNFi therapy. In this aspect, the OSM protein may be detected using one or more antibodies specific for OSM as is described herein, for example, one or more of western blot, ELISA, Proximity Extension Assay, or mass-spectrometrically.

The disclosed methods may employ a variety of different methods for detecting one or more biomarkers and/or quantifying or determining a relative level of one or more biomarkers. The methods may include protein level measurements, DNA measurements, or RNA measurements. Methods for capturing, analyzing, quantifying, etc., biomarkers are known in the art. For example, in one aspect, one or more of the disclosed biomarkers may be captured with capture reagents immobilized to a solid support, such as a biochip or other substrate suitable for such capture, and may include, for example, a glass or plastic in the form of, e.g., a microtiter plate, a stick, a bead, or a microbead. Once captured on a substrate, the marker or markers in a sample may be assayed for presence and/or quantity/abundance. In one aspect, one or more of the disclosed biomarkers may be detected and/or measured by a variety of detection methods including for example, gas phase ion spectrometry methods, optical methods, electrochemical methods, atomic force microscopy and radio frequency methods.

In one aspect, a sample obtained from an individual may be prepared to enhance detectability of one or more biomarkers therein. For example, a blood serum sample may be fractionated using methods known in the art. Examples in include Cibacron blue agarose chromatography and single stranded DNA affinity chromatography, anion exchange chromatography, affinity chromatography (e.g., with antibodies) and the like. Such fractionation may be carried out prior to detection of the biomarker. The method of fractionation may depend on the type of detection method used. Methods that enriches for the protein of interest can be used. Sample preparations, such as pre-fractionation protocols, are optional and may not be necessary to enhance detectability of markers depending on the methods of detection used. In one aspect, biomarkers in a sample may be separated by high-resolution electrophoresis, e.g., one or two-dimensional gel electrophoresis. A fraction containing a marker can be isolated and further analyzed by gas phase ion spectrometry. In another embodiment, two-dimensional gel electrophoresis is used to generate two-dimensional array of spots of biomarkers, including one or more markers.

In one aspect, an immunoassay may be used to detect and analyze a biomarker in a sample. In this aspect, the method may comprise (a) providing an antibody that specifically binds to a marker; (b) contacting a sample with the antibody; and (c) detecting the presence of a complex of the antibody bound to the marker in the sample. For example, an exemplary immunoassay employs an antibody to specifically bind an antigen (e.g., a marker), and uses the specific binding properties of a particular antibody to isolate, target, and/or quantify the antigen. The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. For example, polyclonal antibodies can be selected to obtain only those polyclonal antibodies that are specifically immunoreactive with that marker and not with other proteins, except for polymorphic variants and alleles of the marker. This selection may be achieved by subtracting out antibodies that cross-react with the marker molecules from other species.

In one aspect, the method of detection may employ a labeled detection reagent. For example, the detection reagent may be, e.g., a first or second antibody labeled with a detectable label. Exemplary detectable labels include magnetic beads (e.g., DYNABEADS™), fluorescent dyes, radiolabels, enzymes (e.g., horse radish peroxide, alkaline phosphatase and others commonly used in an ELISA), and colorimetric labels such as colloidal gold or colored glass or plastic beads. Alternatively, the marker in the sample can be detected using an indirect assay, wherein, for example, a second, labeled antibody may used to detect bound marker-specific antibody, and/or in a competition or inhibition assay wherein, for example, a monoclonal antibody which binds to a distinct epitope of the marker may incubated simultaneously with the mixture.

Exemplary methods for measuring the amount of, or presence of, one or more biomarkers include detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Electrochemical methods include voltametry and amperometry methods. Radio frequency methods include multipolar resonance spectroscopy. Methods for performing these assays are known in the art, and may include an enzyme immune assay (EIA) such as enzyme-linked immunosorbent assay (ELISA), a radioimmune assay (RIA), a Western blot assay, or a slot blot assay.

In one aspect, the method may employ an incubation step or a washing step. For example, incubation steps may vary from about 5 seconds to several hours, or from about 5 minutes to about 24 hours. The incubation time will depend upon the assay format, marker, volume of solution, concentrations and the like. The methods may be carried out at ambient temperature, or may be conducted over a range of temperatures, such as 10° C. to 40° C.

In one aspect, the methods employ an immunoassays to determine presence or absence of a marker in a sample, as well as the quantity of a marker in a sample, in which the amount of an antibody-marker complex may be determined by comparing to a standard. A standard can be, e.g., a known compound or another protein known to be present in a sample. The test amount of marker need not be measured in absolute units, as long as the unit of measurement can be compared to a control.

In one aspect, the biomarker is detected, and biomarker data is generated, wherein the data may then analyzed by a computer software program. The software may comprise code that converts signal from the mass spectrometer into computer readable form, and may include code that applies an algorithm to the analysis of the signal to determine whether the signal represents a "peak" in the signal corresponding to a marker as disclosed herein, or other useful markers. The software may also include code that executes an algorithm that compares signal from a test sample to a typical signal characteristic of "normal" one and determines the closeness of fit between the two signals. The software also can include code indicating which the test sample is closest to, thereby providing a probable diagnosis.

Kits

In one embodiment, provided herein are kits comprising reagents for detecting the biomarker levels, wherein the reagents may include antibodies, nucleic acids, which may hybridize to mRNA isolated from a biological sample, and the like. In one aspect, reagents may be labelled, or in another embodiment nucleic acids isolated from a biological sample are labelled. In another embodiment, the kit provides instructions for detecting the label qualitatively or quantitatively. In another aspect, disclosed are kits for using the disclosed biomarkers which further include assays and analytical tools for the assays, such as one or more of reagents, standards and instructions for analyzing the expression level of one or more biomarkers in a biological sample.

In one aspect, the kit may comprise a buffering agent, a preservative, or a protein stabilizing agent, an enzyme, or a substrate. The substrate may be a means of detecting a label, or the expressed protein product itself. In one aspect, the kit may comprise reagents that may be necessary for detection of nucleic acids, amino acids or hybridization signals for nucleic acids.

In one aspect, the results obtained may be compared to a standard, which, in another aspect, may comprise a series of standards, which, in another aspect may be used in the kits for quantification of differential levels of the biomarker or differential expression. In one aspect, the standard may comprise antibodies for detecting a standard biomarker. In one aspect, the standard may comprise nucleic acids when the kit is used for the determination of nucleic acid profile, or in another aspect the standard is a protein when the kit is used for the determination of expressed protein profile.

In one aspect, the kit may be adapted for high-throughput screening, and comprise a microarray. In one aspect, the kit may comprise a microarray, which may comprise cRNA of the genes indicated, and others. In one aspect, the kit may comprise standard oligonucleotide probes, PCR reagents and detectable labels.

In one embodiment, the kit further may comprise a positive and negative control, wherein said standards can be assayed and compared to the test sample.

Kits that include one or more reaction vessels that have aliquots of some or all of the reaction components of the invention in them may be provided. Aliquots can be in liquid or dried form. Reaction vessels can include sample processing cartridges or other vessels that allow for the containment, processing and/or amplification of samples in the same vessel.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus may be considered to constitute examples of modes for its practice. However, those of skill in the art should, in light of the present disclosure, appreciate that many changes may be made in the specific embodiments that are disclosed and still obtain a like or similar result without departing from the spirit and scope of the invention.

As stated above, therapeutic options for moderate-to-severe Crohn disease (CD) include monoclonal antibodies (mAb) that antagonize circulating or tissue-bound inflammatory cytokines and leukocyte recruitment pathways. Following the pivotal REACH study,[1] mAb's targeting tumor necrosis factor-alpha (anti-TNF) have become and remain the most commonly used first-line biologic agents for children with moderate-to-severe CD. Despite high rates of clinical response to anti-TNF (75%-88.4%),[1,2] many children and adults continue to experience symptom flares and serious disease complications as rates of mucosal healing range between 36% and 46% with only 19%-36% achieving deep remission (both clinical remission and mucosal healing).[3,4] Although rates of deep remission are likely to improve with increased utilization of personalized anti-TNF dosing regimens[5] and effective dose optimization strategies following proactive therapeutic drug monitoring,[6] a sizable percentage of children will continue to fail anti-TNF despite adequate drug exposure.

Despite the heterogeneity of CD phenotypes and a potentially aggressive course of inadequately treated CD, treatment selection is currently based on clinical factors that poorly define CD subtype (mainly, the potential for a structuring or fistulizing phenotype). Previous studies to evaluate baseline predictors of anti-TNF nonresponse have found that older age,[3] very early onset disease,[4] history of smoking,[7] and history of a CD-related surgery[3] are clinical risk factors for poor response. Further studies have found that c-reactive protein,[8] hypoalbuminemia, and low TREM19 are associated with poor response. As new biologics are available, there has been renewed interest for an anti-TNF companion diagnostic as associations between molecular inflammatory signatures (tissue-based) and anti-TNF response have also been discovered.[10-12]

It has been recently found that Oncostatin M (OSM) and OSM receptor (OSMR) are highly expressed in the inflamed intestinal tissue in newly diagnosed, treatment-naive pediatric CD patients.[12] Moreover, hierarchical clustering was performed to discover additional cytokines and chemokines that were associated with a high intestinal expression of OSM (referred to as the $OSM^{high}$ module). Remarkably, West et al found that patients within the $OSM^{high}$ module were largely (90%) infliximab refractory with a significant correlation between elevated OSM and need for surgery.[12] The authors of this study, however, did not report on plasma OSM and anti-TNF outcomes. Applicant has previously found that the ileal and rectal mRNA expression of Fcγ receptor IA (FCGRIA) was up to 3-fold higher in new diagnosis, treatment-naive CD compared with controls.[13] Applicant has subsequently found similar elevations in peripheral blood neutrophil FCGRIA (nCD64) in treatment-naive pediatric CD patients.[13,14] nCD64 expression was also found to correlate with endoscopic severity,[14] while elevations in nCD64 is a significant risk factor for treatment relapse in silent (asymptomatic) CD.[15] Although intestinal FCGRIA mRNA expression was found to be upregulated in infliximab nonresponders,[16] peripheral blood nCD64 expression and anti-TNF outcomes have not been previously investigated. With a goal to develop a noninvasive, blood-based companion diagnostic for anti-TNF refractory CD, Applicant hypothesized that increases in plasma OSM would also be associated with early and late anti-TNF nonresponse.

Materials and Methods

Patient Recruitment. Applicant performed a pilot investigation of CD patients enrolled in the Clinical and Molecular Signature to Predict Response to Anti-TNF Therapy in Pediatric IBD (PROSE) study. PROSE is a single-center, inception cohort of children and young adults (≤22 y old) with inflammatory bowel disease (IBD) who enrolled immediately prior to starting infliximab at Cincinnati Children's Hospital Medical Center between July 2014 and October 2018. Participants were prospectively monitored for treatment response with longitudinal biospecimens collected for 1 year. All patients enrolled were anti-TNF naive, and their infliximab dose and frequency were determined by the treating provider.

Study Outcomes. The primary outcome measure was pretreatment plasma OSM concentration and the start of maintenance (week 12 [W12]) biochemical response defined as >50% reduction from the patient's baseline fecal calprotectin.[17] Secondary outcomes included pretreatment plasma OSM concentration or nCD64 and biochemical remission at either W12 or week 52 (W52; fecal calprotectin < 250 µg/g[18, 19]). Clinical remission was assessed with the weighted pediatric CD activity index (wPCDAI) and defined as a wPCDAI <12.5.[20] The mathematically wPCDAI combines subjective clinical evaluation (abdominal pain, stool frequency, and general well-being) and laboratory tests (albumin and erythrocyte sedimentation rate) with physical exam assessments (weight, perirectal disease, and evaluation of extraintestinal manifestations) and has been shown to correlate with mucosal inflammation.[21] For analysis of the primary outcome, patients who (a) failed to provide stools samples prior to either infusion1/infusion4 or (b) had a baseline fecal calprotectin <250 µg/g were excluded.

Biologic Assays. Plasma OSM concentrations were determined by an enzyme-linked immunosorbent assay (ELISA; Thermo Scientific, MA) from blood samples collected at infusion1 and infusion4. The ELISA has an upper detection limit of 1000 pg/mL, lower detection limit of 1 pg/mL at 1:2 dilution, and an intra-assay coefficient variation (CV) <12%. Whole blood nCD64 was measured by quantitative flow cytometry on a FACS Calibur (BD Biosciences, San Jose, Calif.) using the Leuko64 assay kit (Trillium Diagnostics, Brewer, Me.). The kit includes fluorescent beads and antibodies to CD64 and CD163. The lymphocyte, monocyte, and granulocyte populations are defined by their forward and side scatter characteristics with CD163 staining to further define the monocyte population. The neutrophil CD64 index is the result of the ratio of the mean fluorescent intensity of the granulocytes to that of the calibration beads. Fecal calprotectin was measured from stool samples collected prior to infusion1 and infusion4 utilizing an ELISA kit with an intra-assay CV of 2.6%-10.5% (Buhlmann, Switzerland).[22] Trough infliximab concentrations were determined with IDKmonitor (Immundiagnostik, Germany) from stored plasma samples collected immediately prior to the fourth infliximab infusion. The presence of antibodies to infliximab was not assayed. The infliximab ELISA has an upper detection limit of 45 µg/mL, lower detection limit of 0.7 µg/mL at 1:200 dilution, and an intra-assay CV of 1.8%-9.7%.23

Statistical Analysis. Continuous variables are represented as means with SD or as medians with interquartile range (IQR) depending on data distribution. Plasma OSM concentrations at infusion1 were compared between biochemical responders and nonresponders using the Mann-Whitney test. The optimal pre-infliximab OSM concentration cut point was determined for biochemical nonresponse using the Youden index from the receiver-operating characteristic (ROC) curve. The area under the ROC curve (AUC) with 95% confidence intervals (CI), sensitivity, specificity, positive predictive value, and negative predictive value for OSM concentrations were determined for biochemical nonresponse. Applicant utilized this new cut point to define $OSM^{low}$ and $OSM_{high}$. Rates of biochemical response and remission at W12 and W52 were compared by OSM status (low/high) using the Fisher exact test. Pre-infliximab (baseline) categorical variables were assessed for significance for biochemical response and remission using a univariate logistic regression analysis. To reduce the risk of overfitting, the multivariate regression analysis only evaluated OSM and nCD64. Finally, a Kaplan-Meier survival analysis was performed to evaluate the association between the intensity of the blood biomarkers ($OSM_{high}$/$nCD64_{high}$) and time to an unfavorable treatment outcome (surgery or discontinuation of infliximab). A P value of <0.05 was considered statistically significant. All statistical analyses were performed using PRISM version 7 (GraphPad, San Diego, Calif.) and R version 3.4.3 (R Development Core Team, Austria).

Results

Plasma OSM was measured immediately prior to the first infliximab infusion from 40 consecutively enrolled anti-TNF naive CD patients. The mean (SD) age was 13 (4) years old, with 35% female and 5% had a preceding CD-related surgery prior to starting infliximab. Sixty-five percent of the cohort started infliximab within 90 days of diagnosis and the median (IQR) pre-infliximab fecal calprotectin was 1519 µg/g (767-2501). One patient was receiving an immunomodulator in combination with infliximab during induction. Additional patient demographics and disease characteristics are listed in Table 1.

TABLE 1

Clinical Characteristics and Baseline Laboratory Results.
IMM, immunomodulator; BMI, body mass index; ESR, erythrocyte sedimentation rate; CRP, c-reactive protein.

| | |
|---|---|
| Number of patients, N | 40 |
| Female, n (%) | 14 (35) |
| White race, n (%) | 36 (90) |
| Age at first infusion, y (mean, SD) | 13 (4) |
| Disease duration, d (median, IQR) | 43 (18-240) |
| <90 d, n (%) | 26 (65) |
| Previous surgery, n (%) | 2 (5) |
| Concomitant IMM, n (%) | 1 (2.5) |
| Concomitant prednisone, n (%) | 20 (50) |
| Crohn location | |
| Ileal only, n | 4 |
| Colon only, n | 4 |
| Ileocolonic, n | 32 |
| Crohn behavior | |
| Inflammatory, n | 32 |
| Stricturing, n | 6 |
| Penetrating, n | 1 |
| Both stricturing/penetrating, n | 1 |
| Perianal Crohn, n (%) | 10 (25) |
| BMI, kg/m² (median, IQR) | 17.3 (15.2-20.9) |
| BMI z-score (mean, SD) | −0.71 (1.2) |
| wPCDAI (mean, SD) | 43 (28) |
| ESR, mm/h (median, IQR) | 18 (10-26) |
| CRP, mg/dL, (median, IQR) | 1.1 (0.42-2.2) |
| Albumin, g/dL (mean, SD) | 3.4 (0.5) |
| Neutrophil CD64 index (median, IQR) | 1.3 (0.92-1.84) |
| Fecal calprotectin, µg/g (median, IQR) | 1519 (767-2501) |

Elevated Plasma OSM is Associated with Early Biochemical Nonresponse

Figure 1A:
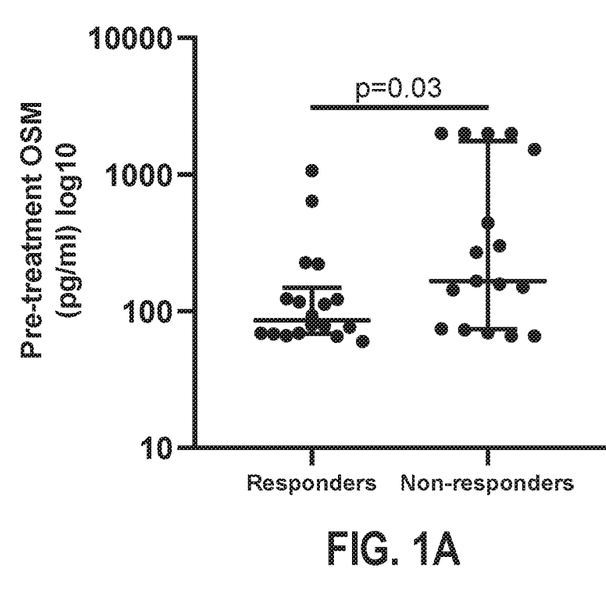
(FIG. 1A) Pre-infliximab plasma OSM concentrations (pg/mL) were evaluated between biochemical responders (>50% reduction in baseline fecal calprotectin) and nonresponders with the Mann-Whitney test (data are log-transformed).
Figure 1B:
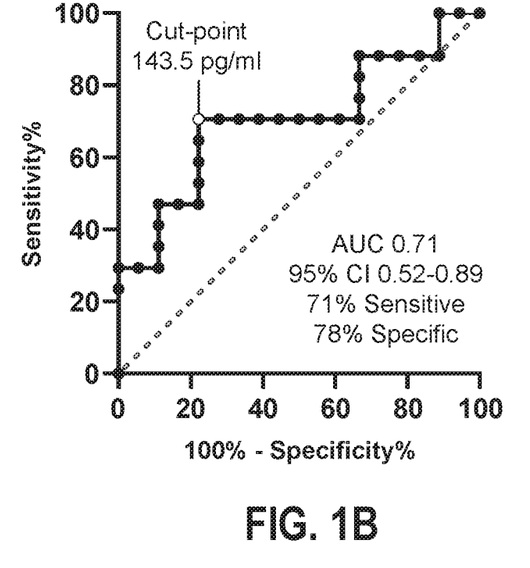
(FIG. 1B) Receiver-operating characteristic analysis was then performed to identify the pre-infliximab OSM cut point (Youden index) that was associated with biochemical nonresponse.

The primary analysis was performed from the 35 patients who provided fecal samples prior to starting infliximab and prior to the first maintenance dose. Applicant found 51.4% (18/35) and 34.3% (12/35) of the cohort achieved biochemical response and biochemical remission at W12, respectively. The median pre-infliximab plasma OSM was 86 pg/mL (69-148) in biochemical responders and 166 pg/mL (74-1766) in biochemical nonresponders (P=0.03, FIG. 1A). By performing a ROC curve analysis and subsequently calculating the Youden index, Applicant established a pre-infliximab OSM >143.5 pg/mL was 71% sensitive and 78% specific with a 75% positive predictive value and a 74% negative predictive value for primary biochemical nonresponse (AUC 0.71, 95% CI 0.52-0.89, FIG. 1B). The median pre-infliximab plasma OSM was 78 pg/mL (68-199) in biochemical remitters (fecal calprotectin <250 μg/g) compared with 150 pg/mL (74-444) in nonremitters (P=0.066). In contrast to biochemical responders, the pre-infliximab OSM cut point that distinguished early (W12) biochemical remitters from nonremitters was 117 pg/mL (AUC 0.69, 95% CI 0.5-0.89).

pg/mL; OR 8.4) were significantly associated with biochemical nonresponse. Pre-infliximab hypoalbuminemia (OR 19, P=0.002), nCD64$_{high}$ (OR 8.9, P=0.011), and OSM$_{high}$/nCD64$_{high}$ (OR 11, P=0.034) were associated with biochemical nonremission. In a multivariate regression evaluating the relationship between biochemical nonremission and nCD64 and OSM, only baseline nCD64$_{high}$ (P=0.017) was independently associated with a pre-maintenance (W12) fecal calprotectin >250 μg/g.

TABLE 2

Comparison of Baseline Disease Characteristics and Laboratory Tests Between Pre-infliximab OSM$^{low}$ (<143.5 pg/mL) and OSM$^{high}$

| Baseline Characteristics | OSM$^{low}$ (n = 23) | OSM$^{high}$ (n = 17) | P |
|---|---|---|---|
| Age at start of infliximab, y (mean, SD) | 13.6 (3.7) | 12.8 (4.7) | 0.57 |
| Time with Crohn, d (median, IQR) | 65 (25-226) | 35 (14-280) | 0.50 |
| BMI z-score (mean, SD) | −1.0 (1.2) | −0.24 (1.1) | 0.041 |
| Surgery before anti-TNF, n (%) | 2 (8.7%) | 0 | 0.50 |
| Starting infliximab dose, mg/kg (median, IQR) | 5.9 (5-6.8) | 6.3 (5.8-9.2) | 0.08 |
| wPCDAI (median, IQR) | 40 (20-60) | 40 (18-74) | 0.59 |
| CRP, mg/dL (median, IQR) | 0.71 (0.28-1.6) | 1.4 (0.95-3.4) | 0.062 |
| Albumin, g/dL (mean, SD) | 3.4 (0.4) | 3.3 (0.5) | 0.21 |
| Fecal calprotectin, μg/g (median, IQR) | 1383 (743-2501) | 1656 (817-2501) | 0.38 |

OSM$^{low}$ is Associated Higher Rates of Biochemical and Clinical Remission

Figure 2A:
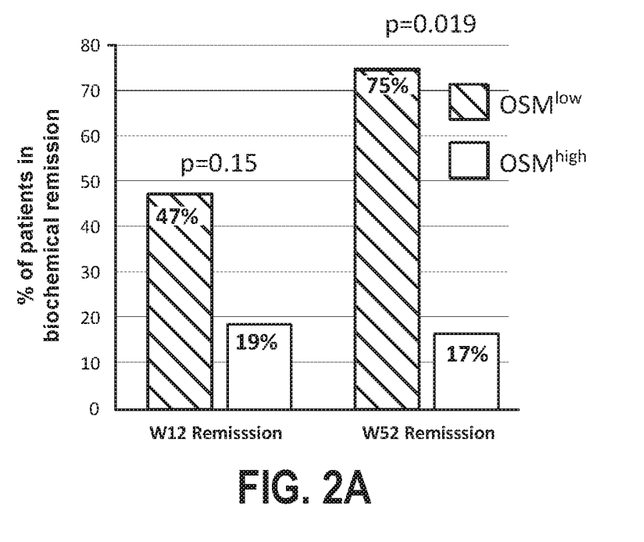
(FIG. 2A) $OSM^{low}$ patients had a higher rate of W52 biochemical remission (fecal calprotectin <250 µg/g) and (FIG. 2B) clinical remission (wPCDAI <12.5) compared with $OSM_{high}$. Rates of remission were compared by the Fisher exact test.
Figure 2B:
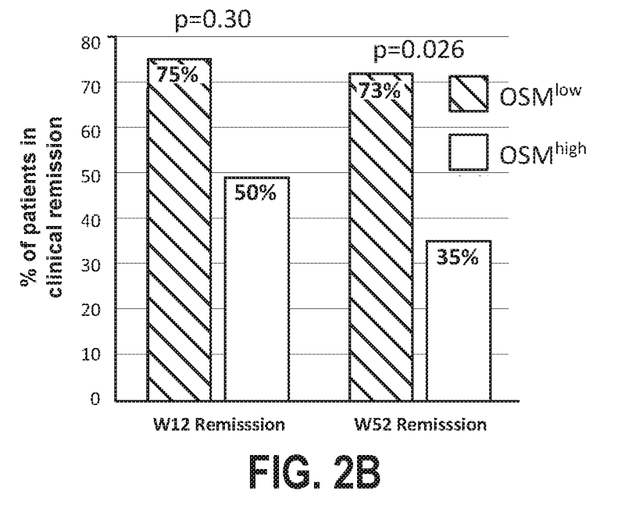

Utilizing the above cut point for early biochemical response, Applicant defined OSM$^{low}$ as a pre-infliximab OSM <143.5 pg/mL. Applicant found no difference in rates of early (W12) biochemical and clinical remission between OSM$^{low}$ and OSM$^{high}$ patients. At 1 year, however, OSM$^{low}$ patients had significantly higher rates of both W52 biochemical and clinical remission (FIG. 2A-2B). In a subset of these 35 patients who also had a fecal calprotectin collected at W52 (n=20), Applicant found the median pre-infliximab plasma OSM was 77 pg/mL (66-117) in W52 biochemical remitters compared to a median OSM of 444 pg/mL (186-2001) in nonremitters (P=0.004). The cut point for baseline OSM that was associated with W52 biochemical nonremission was >222 pg/mL (AUC 0.88, 95% CI 0.72-1.0, 77% sensitive, 100% specific).

Elevated Pretreatment nCD64 is Associated with Biochemical Nonremission

Figure 3A:
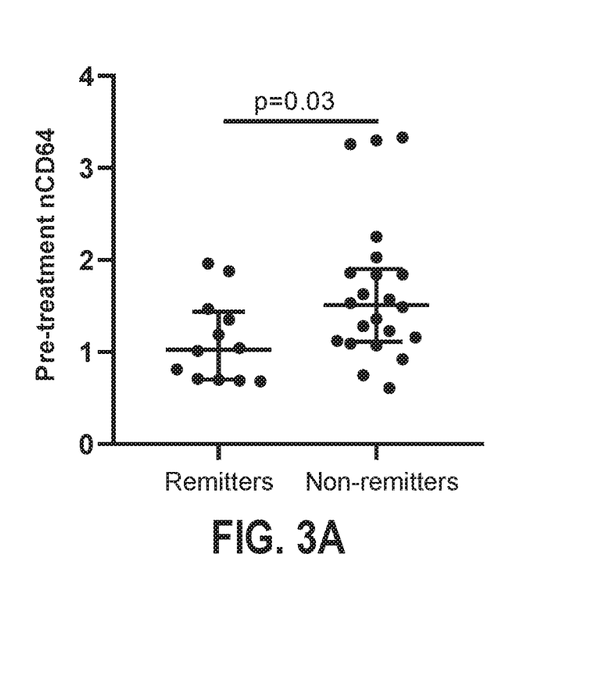
(FIG. 3A) Evaluation of pre-infliximab whole blood neutrophil CD64 surface expression (nCD64) between biochemical remitters (fecal calprotectin <250 µg/g) and nonremitters at the end of induction with the Mann-Whitney test.
Figure 3B:
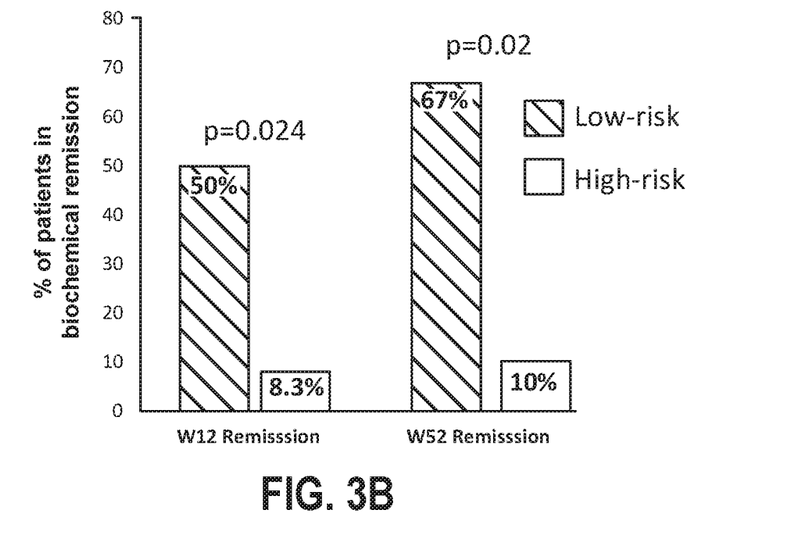
(FIG. 3B) Study participants were classified as high risk ($OSM_{high}$/$nCD64_{high}$) based on their pretreatment plasma OSM and nCD64 concentrations. High-risk patients had lower rates of biochemical remission at the end of induction (W12) and at W52 compared with the low-risk group. Rates of remission were compared by the Fisher exact test.

Applicant found the median (IQR) nCD64 was 1.03 (0.7-1.4) in early biochemical remitters compared with 1.5 (1.1-1.9) in biochemical nonremitters (P=0.03, FIG. 3A). ROC curve analysis and subsequent Youden index defined nCD64$_{high}$ as 1.07 (AUC 0.73, 95% CI 0.54-0.92). Although there was no correlation between OSM and nCD64 (Spearman r=0.23, P=0.17), patients with a combination of OSM$^{high}$ and nCD64$_{high}$ (classified as "high risk") was associated with poor early and late biochemical outcomes (FIG. 3B). The high-risk classification included 33% of the cohort.

Baseline Predictors of Early Biochemical Outcomes

Baseline disease characteristics between OSM$^{low}$ and OSM$^{high}$ patients were similar, with only the pre-infliximab BMI z-score statistically different (Table 2). Next, Applicant evaluated pretreatment predictors of poor (early) biochemical outcomes using a univariate regression analysis. After evaluating multiple pretreatment predictors of early nonresponse (Table 3), Applicant found baseline hypoalbuminemia (≤3.5 g/dL; odds ratio [OR] 6.2) and OSM$^{high}$ (>143.5

TABLE 3

Pretreatment Predictors of Early (Premaintenance) Biochemical Outcomes

| Baseline Characteristic | Odds Ratio | 95% CI | P |
|---|---|---|---|
| Biochemical nonresponse (<50% reduction from baseline fecal calprotectin) | | | |
| ≤10-y-old starting infliximab | 1.9 | 0.44-9.1 | 0.40 |
| wPCDAI >40 | 0.9 | 0.23-3.4 | 0.88 |
| ESR ≥20 mm/h | 15 | 0.33-7.5 | 0.58 |
| CRP ≥5 mg/dL | 5.5 | 0.72-115 | 0.15 |
| Albumin ≤3.5 g/dL | 6.2 | 1.2-48 | 0.042 |
| OSM$^{high}$ (≥143.5 pg/mL) | 8.4 | 2-43 | 0.006 |
| nCD64$^{high}$ (>1.07) | 2.8 | 0.61-15 | 0.21 |
| OSM$^{high}$ + nCD64$^{high}$ | 13.3 | 2.6-106 | 0.005 |
| Biochemical nonremission (fecal calprotectin >250 μg/g) | | | |
| Albumin ≤3.5 g/dL | 19 | 3.4-165 | 0.002 |
| OSM$^{high}$ (≥143.5 pg/mL) | 3.9 | 0.90-21 | 0.084 |
| nCD64$^{high}$ (>1.07) | 8.9 | 1.8-55 | 0.011 |
| OSM$^{high}$ + nCD64$^{high}$ | 11 | 1.7-219 | 0.034 |

CRP, c-reactive protein; ESR, erythrocyte sedimentation rate.

Delta OSM and nCD64 During Induction

Figure 4A:
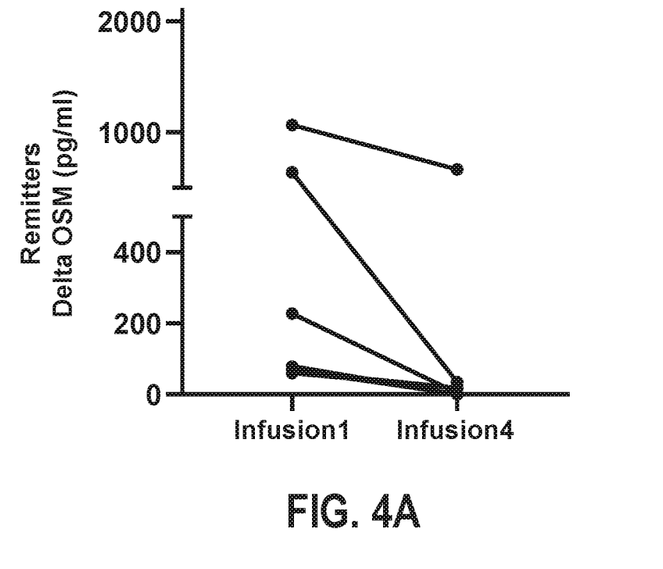
(FIG. 4A) The absolute change (delta) in plasma OSM between pre-infliximab (infusion1) and pre-maintenance (infusion4) in patients with early biochemical remission and (FIG. 4B) biochemical nonremission. The one patient with an increase in plasma OSM from baseline to W12 had surgery for an ileal stricture 4 months after starting infliximab.
Figure 4B:
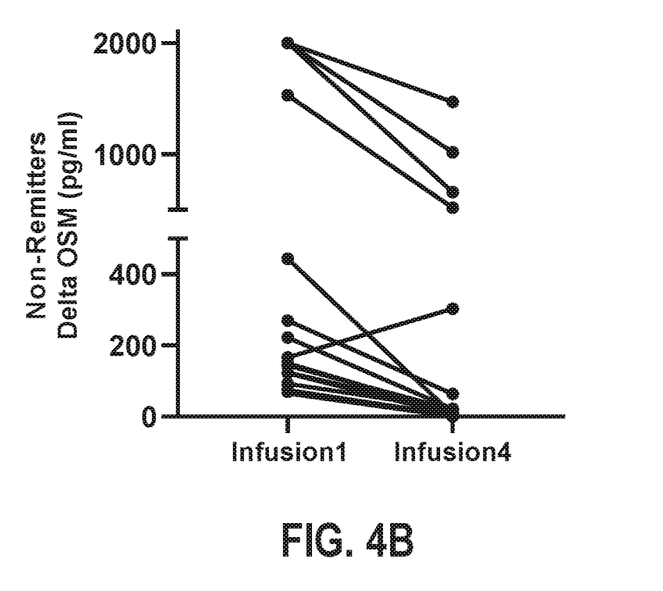
Figure 4C:
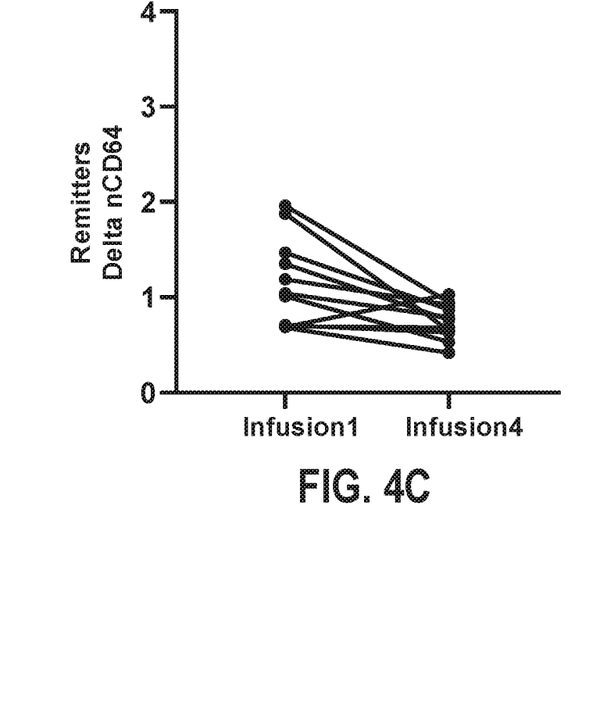
(FIG. 4C) The absolute change in nCD64 between pretreatment and pre-maintenance in patients with early biochemical remission and (FIG. 4D) biochemical nonremission.
Figure 4D:
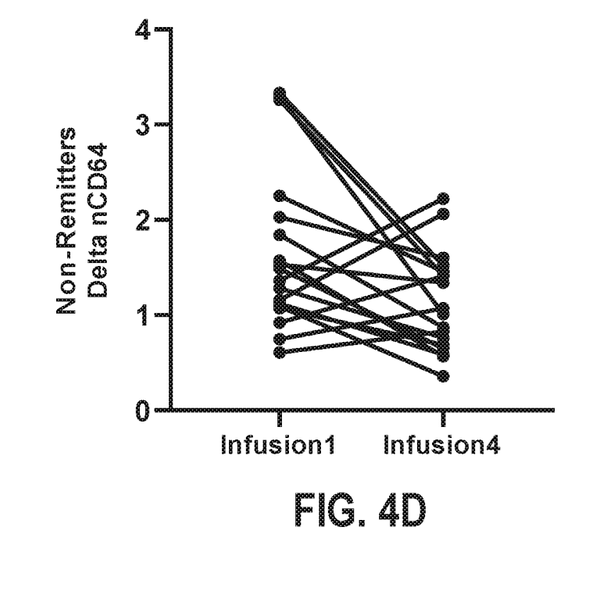

Applicant found the median reduction (percent change) in OSM from pretreatment to pre-maintenance was higher in biochemical remitters compared with nonremitters (P=0.09). FIGS. 3A and B demonstrates the change in plasma OSM from baseline (infusion1) to pre-maintenance (W12) in remitters and non-remitters respectively. Plasma OSM was undetectable by the end of induction in 45.5% of the biochemical remitters compared to 21.1% of nonremitter (P=0.23). It is noteworthy that all 6 (100%) patients with an W12 OSM >143.5 pg/mL (OSM$_{high}$) had evidence of active CD at W52. The one patient with an increase in plasma OSM from baseline to W12 went on to have an ileocecal resection for an ileal stricture 4 months after starting infliximab. Applicant also found that the median reduction (infusion1 to infusion 4) for nCD64 was higher in biochemical responders compared with nonresponders (P<0.05). Although there was no difference in the delta nCD64 percent reduction between remitters and nonremitters (P=0.84), FIGS. 4C and D demonstrates an overall lower baseline nCD64 in remitters compared with nonremitters.

Additional Outcomes

Figure 5A:
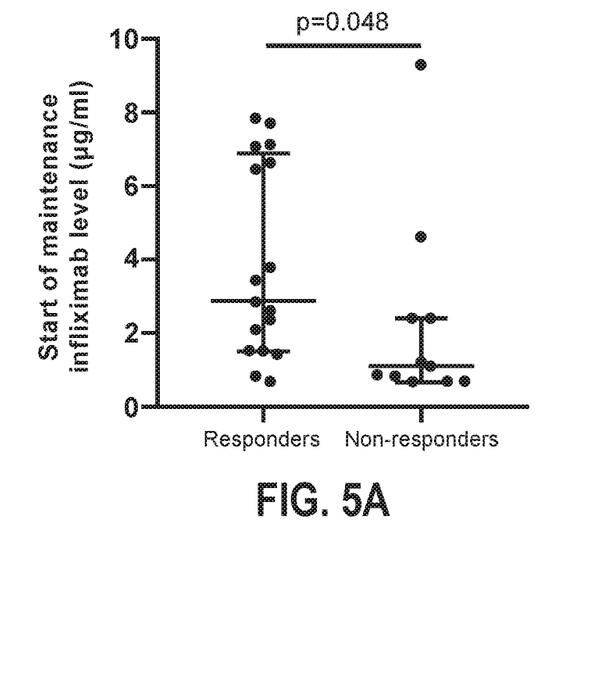
Figure 5B:
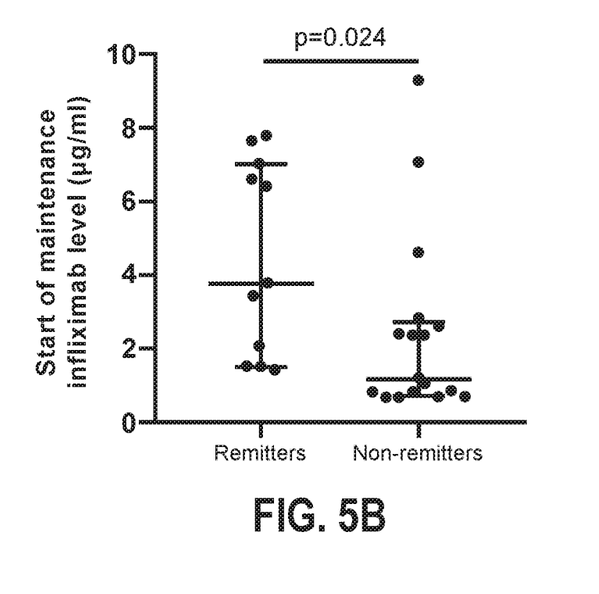
Figure 5C:
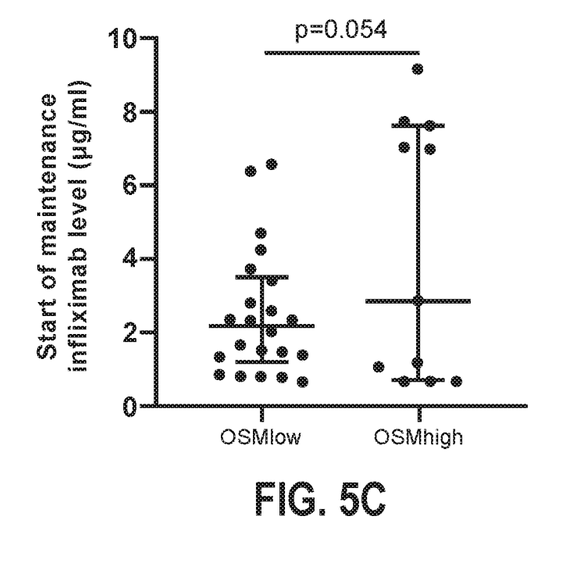
(FIG. 5C) W12 infliximab concentration was also compared between pre-treatment $OSM^{low}$ and $OSM^{high}$ patients. All comparisons were performed with the Mann-Whitney test.

One year from starting infliximab, 87.5% of the cohort was receiving infliximab while 12.5% had a CD-related surgery. In a survival curve analysis, Applicant found there was no association between OSM, nCD64 or the combination OSM/nCD64 status and time to a poor outcome (time to surgery and/or time to infliximab discontinuation; data not shown). As expected, Applicant found biochemical responders and remitters had higher median infliximab concentrations prior to the fourth infusion compared with nonresponders (P=0.048) and nonremitters (P=0.024, FIGS. 5A and 5B), respectively. Applicant did not find a difference in the median (IQR) W12 infliximab concentrations between pretreatment $OSM^{low}$ and $OSM^{high}$ patients (FIG. 5C).

Discussion

Approximately 80% of pediatric CD patients treated with anti-TNF will have an early clinical response.[1, 2] However, recent data strongly support the attainment of mucosal healing as a major treatment target in pediatric and adult-onset CD. In pediatric CD, rates of mucosal healing after 1 year of anti-TNF range from 39% to 63%.[24, 25] Rates of mucosal healing in adults with CD receiving optimized anti-TNF dosing regimens range from 27% to 40%[5, 26] further indicating a larger than expected subset of anti-TNF responders in both pediatric and adult-onset CD. With novel CD therapies now available, there is a critical need for the development of a companion diagnostic for all biologics (including anti-TNF) to provide guidance to clinicians for the initial treatment selection as long-term efficacy may be affected by the first biologic exposure.[27] Respectively, West et al and Wojtal et al found increased intestinal expression of OSM[12] and FCGRIA[16] were associated with anti-TNF nonresponse. In Applicant's study, elevations in pretreatment plasma OSM and whole blood nCD64 were found to associate with unfavorable (early and late) biochemical outcomes to infliximab.

OSM is part of the IL-6 cytokine family that following binding to the OSM receptor (OSMR) functions to induce downstream signaling pathways such as signal transducer and activator of transcription 3, mitogen-activated protein kinase, and phosphatidylinositol-3-kinase.[12] Functional processes of OSM include a role in the inflammatory response, hematopoiesis, tissue remodeling (liver repair, cardiac tissue remodeling), and osteoclastogenesis.[28] Overproduction of OSM has been associated with skin and lung inflammation, atherosclerosis and several forms of cancer.[28] West et al identified expression of OSM and OSMR from intestinal mucosal biopsies is increased in active CD and ulcerative colitis (UC).[12] Utilizing data derived from Gene Expression Omnibus (GEO) data sets (162 CD and 42 controls),[29] West et al reported intestinal OSM was especially enriched in CD patients with deep mucosal ulcerations.[12] Interestingly, although there was no correlation between OSM expression and traditional clinical or laboratory markers of disease severity, they did find a correlation between intestinal OSM expression and need for early IBD surgery.[12] In the investigation, patients that were grouped into an $OSM^{high}$ expression module (based on the expression of OSM-associated genes) had a higher likelihood of primary nonresponse to anti-TNF therapy. They found only 10%-15% in the $OSM^{high}$ module achieved complete (early) mucosal healing compared to 69%-85% of patients in the $OSM^{low}$ module.[12]

Previous studies investigating baseline predictors of anti-TNF nonresponse have mainly focused on clinical (demographics, disease phenotype) characteristics and intestinal gene expression.[10, 11] In a large cohort of adult-onset CD, Vermeire et al found older age, isolated ileitis, and previous history of CD surgery were associated with infliximab nonresponse.[3] In addition, infliximab response has been associated with a c-reactive protein >5 mg/L in adult-onset CD.[8] In pediatric CD, favorable, early anti-TNF response has been associated with postinduction reductions in fecal calprotectin,[17] improvements in wPCDAI,[24] and higher infliximab concentrations[30-32]; however, none of these studies identified baseline laboratory tests associated with nonresponse. In addition, in a multivariable analysis of primary nonresponse conducted in a large cohort of 955 CD patients treated with infliximab, low infliximab concentration at week 14 (OR 0.35, 95% CI 0.20-0.62) was the only independent factor with a concentration of 7 μg/mL as the optimal week 14 drug target associated with remission at week 14 and week 54.[32]

More recently, smaller studies have evaluated blood biomarkers as predictors of CD complications (stricturing), however, not specific to anti-TNF response. In an observational study, Wu et al found elevated extracellular matrix protein 1, ASCA IgA, and CBir levels were associated future conversion from an inflammatory phenotype (B1) to a fibrostenotic phenotype (B2).[33] Similarly, elevation of collagen type III alpha 1 chain and autoantibodies against colony-stimulating factor 2 were associated with development of intestinal strictures in pediatric patients with CD.[34]

To Applicant's knowledge, no other study has evaluated the relationship between pretreatment plasma OSM and outcomes with anti-TNF in IBD patients. Verstockt et al prospectively followed 54 IBD (24 CD and 30 UC) starting anti-TNF.[35] They found anti-TNF endoscopic responders (in CD, SES-CD ≤2; in UC, Mayo endoscopic subscore ≤1) had a decrease in triggering receptor expressed on myeloid cells 1 (TREM1) expression from whole blood RNA with a similar reduction in mucosal TREM1 and OSM gene expression (obtained from inflamed intestinal biopsies).[35] Although the authors reported whole blood relative OSM expression (using qPCR) was higher (fold-change 0.67) in nonremitters, the relative OSM expression was not statistically different compared with remitters (P=0.09). In the study, serum TREM1 was measured with ELISA, while OSM was quantified with whole blood gene expression. In Applicant's study, not only was the pretreatment plasma OSM associated with infliximab outcomes, but Applicant's results suggest that longitudinal OSM assessments may be beneficial for monitoring disease activity as persistent elevations in OSM beyond W12 were associated with continued CD inflammation at W52.

Applicant has previously found that nCD64 strongly correlates with endoscopic-defined CD severity[14] with FCGRIA expression >3-fold higher in the intestinal tissue of treatment-naive, newly diagnosed pediatric CD compared with controls.[13, 29] Although nCD64 was shown to be effective in identifying silent CD (asymptomatic patients with ongoing intestinal inflammation who are at high risk of clinical relapse),[15] Applicant has not analyzed nCD64 as a companion diagnostic for anti-TNF therapy. However, one previous study found that colonic FCGRIA expression from the inflamed bowel was significantly upregulated in patients failing anti-TNF.[16] This is believed to be the first study to show that elevations in pretreatment nCD64 (alone and in combination with elevated plasma OSM) were strongly associated with poor biochemical outcomes in patients receiving infliximab. Additional studies are ongoing to understand the potential mechanisms of increased nCD64 expression and anti-TNF nonresponse.

The strengths of the study include enrolling a prospectively monitored cohort of children and young adults with CD who predominantly received infliximab monotherapy in a real-world setting. Applicant's goal was to evaluate pretreatment biomarkers with multiple treatment outcomes (including clinical and biochemical response) as it was not feasible to perform repeat endoscopy with Applicant's observational study. As plasma OSM has not been studied in the IBD population, multiple ROC curve analyses were planned to identify potential OSM cut points for early/late biochemical nonresponse and nonremission. Conclusions are based on plasma OSM obtained from a CD cohort that largely consisted of newly diagnosed CD patients as 65% of the patients started infliximab within 90 days of diagnosis.

Applicant's primary outcome for this study was biochemical response utilizing fecal calprotectin as a surrogate for repeat endoscopy. Although there is little consensus and a paucity of data identifying fecal calprotectin cut points post-induction, Applicant defined biochemical response as a >50% reduction in baseline fecal calprotectin as this cutoff was shown to reliably predict disease inactivity following infliximab induction in a pediatric cohort.[17] Given the dynamic range of fecal calprotectin (50-2500 µg/g) for most commercial laboratories, a reasonable cut point may be established during induction for both fecal calprotectin and lactoferrin to prevent early anti-TNF discontinuation in patients who achieve clinical remission but continue to have mild elevations of the fecal biomarkers.

Conclusion

The Food and Drug Administration defines a companion diagnostic as a device that can identify patients most likely to benefit from a therapy or a device to monitor response with the purpose to adjust the treatment to achieve improved effectiveness. Although intestinal tissue companion diagnostics have previously been viewed as the preferred method to predict response,[10, 12, 36] blood biomarkers are more convenient to collect in daily practice and much less invasive than colonoscopy. In conclusion, pre-infliximab $OSM_{high}$ is associated with early biochemical nonresponse and late (W52) clinical and biochemical nonremission. Pretreatment $nCD64_{high}$ was associated with biochemical nonremission. Thus, clinicians may evaluate pretreatment OSM and nCD64 prior to starting anti-TNF to determine those patients who may benefit from proactive therapeutic drug monitoring, higher starting doses, and more frequent disease activity monitoring.

REFERENCES

1. Hyams J, Crandall W, Kugathasan S, et al.; REACH Study Group. Induction and maintenance infliximab therapy for the treatment of moderate-to-severe Crohn's disease in children. Gastroenterology. 2007; 132:863-873; quiz 1165.
2. Hyams J S, Griffiths A, Markowitz J, et al. Safety and efficacy of adalimumab for moderate to severe Crohn's disease in children. Gastroenterology. 2012; 143:365-374.e2.
3. Vermeire S, Louis E, Carbonez A, et al.; Belgian Group of Infliximab Expanded Access Program in Crohn's Disease. Demographic and clinical parameters influencing the short-term outcome of anti-tumor necrosis factor (infliximab) treatment in Crohn's disease. Am J Gastroenterol. 2002; 97:2357-2363.
4. Kelsen J R, Grossman A B, Pauly-Hubbard H, et al. Infliximab therapy in pediatric patients 7 years of age and younger. J Pediatr Gastroenterol Nutr. 2014; 59:758-762.
5. Colombel J F, Panaccione R, Bossuyt P, et al. Effect of tight control management on Crohn's disease (CALM): a multicentre, randomised, controlled phase 3 trial. Lancet. 2018; 390:2779-2789.
6. Papamichael K, Vajravelu R K, Vaughn B P, et al. Proactive infliximab monitoring following reactive testing is associated with better clinical outcomes than reactive testing alone in patients with inflammatory bowel disease. J Crohns Colitis. 2018; 12:804-810.
7. Arnott I D, McNeill G, Satsangi J. An analysis of factors influencing short-term and sustained response to infliximab treatment for Crohn's disease. Aliment Pharmacol Ther. 2003; 17:1451-1457.
8. Louis E, Vermeire S, Rutgeerts P, et al. A positive response to infliximab in Crohn disease: association with a higher systemic inflammation before treatment but not with −308 TNF gene polymorphism. Scand J Gastroenterol. 2002; 37:818-824.
9. Gaujoux R, Starosvetsky E, Maimon N, et al.; Israeli IBD research Network (IIRN). Cell-centred meta-analysis reveals baseline predictors of anti-TNFα non-response in biopsy and blood of patients with IBD. Gut. 2019; 68:604-614.
10. Arijs I, Quintens R, Van Lommel L, et al. Predictive value of epithelial gene expression profiles for response to infliximab in Crohn's disease. Inflamm Bowel Dis. 2010; 16:2090-2098.
11. Kugathasan S, Denson L A, Walters T D, et al. Prediction of complicated disease course for children newly diagnosed with Crohn's disease: a multicentre inception cohort study. Lancet. 2017; 389:1710-1718.
12. West N R, Hegazy A N, Owens B M J, et al.; Oxford IBD Cohort Investigators. Oncostatin M drives intestinal inflammation and predicts response to tumor necrosis factor-neutralizing therapy in patients with inflammatory bowel disease. Nat Med. 2017; 23:579-589.
13. Minar P, Haberman Y, Jurickova I, et al. Utility of neutrophil Fcγ receptor I (CD64) index as a biomarker for mucosal inflammation in pediatric Crohn's disease. Inflamm Bowel Dis. 2014; 20:1037-1048.
14. Minar P, Jackson K, Tsai Y T, et al. Validation of neutrophil CD64 blood biomarkers to detect mucosal inflammation in pediatric Crohn's disease. Inflamm Bowel Dis. 2017; 24:198-208.
15. Minar P, Jackson K, Tsai Y T, et al. A low neutrophil CD64 index is associated with sustained remission during infliximab maintenance therapy. Inflamm Bowel Dis. 2016; 22:2641-2647.
16. Wojtal K A, Rogler G, Scharl M, et al. Fc gamma receptor CD64 modulates the inhibitory activity of infliximab. PLoS One. 2012; 7:e43361.
17. Zubin G, Peter L. Predicting endoscopic Crohn's Disease activity before and after induction therapy in children: a comprehensive assessment of PCDAI, CRP, and fecal calprotectin. Inflamm Bowel Dis. 2015; 21:1386-1391.
18. D'Haens G, Ferrante M, Vermeire S, et al. Fecal calprotectin is a surrogate marker for endoscopic lesions in inflammatory bowel disease. Inflamm Bowel Dis. 2012; 18:2218-2224.
19. Nancey S, Boschetti G, Moussata D, et al. Neopterin is a novel reliable fecal marker as accurate as calprotectin for predicting endoscopic disease activity in patients with inflammatory bowel diseases. Inflamm Bowel Dis. 2013; 19:1043-1052.
20. Turner D, Griffiths A M, Walters T D, et al. Mathematical weighting of the pediatric Crohn's disease activity index (PCDAI) and comparison with its other short versions. Inflamm Bowel Dis. 2012; 18:55-62.
21. Turner D, Levine A, Walters T D, et al. Which PCDAI version best reflects intestinal inflammation in pediatric Crohn disease? J Pediatr Gastroenterol Nutr. 2017; 64:254-260.
22. Louis E. Fecal calprotectin: towards a standardized use for inflammatory bowel disease management in routine practice. J Crohns Colitis. 2015; 9:1-3.
23. Guiotto C, Daperno M, Frigerio F, et al. Clinical relevance and inter-test reliability of anti-infliximab antibodies and infliximab trough levels in patients with inflammatory bowel disease. Dig Liver Dis. 2016; 48:138-143.
24. D'Arcangelo G, Oliva S, Dilillo A, et al. Predictors of long-term clinical and endoscopic remission in children with Crohn disease treated with infliximab. J Pediatr Gastroenterol Nutr. 2019; 68:841-846.
25. Kang B, Choi S Y, Kim H S, et al. Mucosal healing in paediatric patients with moderate-to-severe luminal Crohn's disease under combined immunosuppression: escalation versus early treatment. J Crohns Colitis. 2016; 10:1279-1286.
26. D'Haens G, Vermeire S, Lambrecht G, et al.; GETAID. Increasing infliximab dose based on symptoms, biomarkers, and serum drug concentrations does not increase clinical, endoscopic, and corticosteroid-free remission in patients with active luminal Crohn's disease. Gastroenterology. 2018; 154:1343-1351.e1.
27. Van Assche G, Vermeire S, Ballet V, et al. Switch to adalimumab in patients with Crohn's disease controlled by maintenance infliximab: prospective randomised SWITCH trial. Gut. 2012; 61:229-234.
28. Tanaka M, Miyajima A. Oncostatin M, a multifunctional cytokine. Rev Physiol Biochem Pharmacol. 2003; 149:39-52.
29. Haberman Y, Tickle T L, Dexheimer P J, et al. Pediatric Crohn disease patients exhibit specific ileal transcriptome and microbiome signature. J Clin Invest. 2014; 124:3617-3633.
30. Singh N, Rosenthal C J, Melmed G Y, et al. Early infliximab trough levels are associated with persistent remission in pediatric patients with inflammatory bowel disease. Inflamm Bowel Dis. 2014; 20:1708-1713.
31. Clarkston K, Tsai Y T, Jackson K, et al. Development of infliximab target concentrations during induction in pediatric Crohn disease patients. J Pediatr Gastroenterol Nutr. 2019; 69:68-74.
32. Kennedy N A, Heap G A, Green H D, et al.; UK Inflammatory Bowel Disease Pharmacogenetics Study Group. Predictors of anti-TNF treatment failure in anti-TNF-naive patients with active luminal Crohn's disease: a prospective, multicentre, cohort study. Lancet Gastroenterol Hepatol. 2019; 4:341-353.
33. Wu J, Lubman D M, Kugathasan S, et al. Serum protein biomarkers of fibrosis aid in risk stratification of future stricturing complications in pediatric Crohn's disease. Am J Gastroenterol. 2019; 114:777-785.
34. Ballengee C R, Stidham R W, Liu C, et al. Association between plasma level of collagen type III alpha 1 chain and development of strictures in pediatric patients with Crohn's disease. Clin Gastroenterol Hepatol. 2019; 17: 1799-1806.
35. Verstockt B, Verstockt S, Dehairs J, et al. Low TREM1 expression in whole blood predicts anti-TNF response in inflammatory bowel disease. Ebiomedicine. 2019; 40:733-742.
36. Tew G W, Hackney J A, Gibbons D, et al. Association between response to etrolizumab and expression of integrin $\alpha$ E and granzyme A in colon biopsies of patients with ulcerative colitis. Gastroenterology. 2016; 150:477-87.e9.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. All accessioned information (e.g., as identified by PUBMED, PUBCHEM, NCBI, UNIPROT, or EBI accession numbers) and publications in their entireties are incorporated into this disclosure by reference in order to more fully describe the state of the art as known to those skilled therein as of the date of this disclosure. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A method of treating an individual having an inflammatory bowel disease ("IBD"), the method comprising:
    a) detecting a pre-tumor necrosis factor (TNF) inhibitor treatment Oncostatin M (OSM) protein concentration in a peripheral blood sample obtained from said individual;

b) detecting a pre-tumor necrosis factor (TNF) inhibitor treatment neutrophil FCGRIA (nCD64) concentration in a peripheral blood sample obtained from said individual;

c) classifying said individual as a TNF inhibitor non-responder or a TNF inhibitor responder, based on said pre-TNF inhibitor treatment plasma OSM level and said pre-TNF inhibitor nCD64 level, wherein:
   i. said individual is classified as a TNF inhibitor non-responder if:
      A. said pre-TNF inhibitor treatment plasma OSM level is greater than or equal to 143.5 pg/ml, and
      B. said nCD64 level is greater than 1.07; and
   ii. said individual is classified as a TNF inhibitor responder if:
      A. said pre-TNF inhibitor treatment plasma OSM level is less than 143.5 pg/ml, and
      B. said nCD64 level is less than 1.07; and d) administering a non-TNF inhibitor treatment to said TNF inhibitor non-responder, or administering TNF inhibitor to said TNF inhibitor responder.

2. The method of claim 1, wherein said IBD is selected from ulcerative colitis (UC) and Crohn's disease (CD).

3. The method of claim 1, wherein said detecting of said OSM protein concentration in said peripheral blood sample comprises contacting said peripheral blood sample with an antibody that specifically binds to OSM protein and measuring an amount of OSM bound to said antibody.

4. The method of claim 1, wherein said detecting of said OSM protein concentration in said peripheral blood sample comprises measuring an amount of an antibody-OSM complex.

5. The method of claim 1, wherein said detecting of said OSM protein concentration in said peripheral blood sample comprises determining OSM concentrations in said peripheral blood sample using an enzyme-linked immunosorbent assay (ELISA) and said peripheral blood sample is serum or plasma.

6. The method of claim 1, further comprising comparing said detected OSM protein concentration to a control, and further normalizing said detected OSM protein concentration to said control.

7. The method of claim 1, wherein said TNF inhibitor is an anti-TNF antibody.

8. The method of claim 1 wherein said TNF inhibitor is an anti-TNF monoclonal antibody.

9. The method of claim 1, wherein said TNF inhibitor is selected from Adalimumab, adalimumab-atto, Certolizumab pegol, Etanercept, Golimumab, Infliximab, Infliximab-axxq, Adalimumab-adaz, infliximab-dyyb, Renflexis, or biosimilar of any of the foregoing TNF inhibitor.

10. The method of claim 1, wherein said individual is characterized as a TNF inhibitor non-responder the method comprising administering one or more active agents selected from vedolizumab, ustekinumab, tofacitinib, mesalamine, budesonide, prednisone, 6-mercaptopurine, azathioprine, methotrexate, and combinations thereof.

11. The method of claim 2, wherein said IBD is Crohn's disease (CD).

12. The method of claim 2, wherein said IBD is ulcerative colitis (UC).

13. The method of claim 1, wherein if said individual is determined to be a TNF inhibitor non-responder, the method comprises administering said non-TNF inhibitor treatment.

14. The method of claim 13, wherein said non-TNF inhibitor treatment comprises administering one or more active agents selected from vedolizumab, ustekinumab, tofacitinib, mesalamine, budesonide, prednisone, 6-marcaptopurine, azathioprine, methotrexate, and combinations thereof.

* * * * *